United States Patent
Tata et al.

(10) Patent No.: US 12,232,691 B2
(45) Date of Patent: Feb. 25, 2025

(54) USER INTERFACE FOR STEERABLE ENDOSCOPE

(71) Applicant: COVIDIEN AG, Neuhausen am Rheinfall (CH)

(72) Inventors: Derek Scot Tata, Longmont, CO (US); Peter Douglas Colin Inglis, Boulder, CO (US); Alexandra Hause, Denver, CO (US); Bo Chen, Louisville, CO (US); Michael Ng, Kowloon (HK); Craig Allen Patton, Boulder, CO (US)

(73) Assignee: Covidien AG (CH)

( * ) Notice: Subject to any disclaimer, the term of this patent is extended or adjusted under 35 U.S.C. 154(b) by 644 days.

(21) Appl. No.: 17/081,621

(22) Filed: Oct. 27, 2020

(65) Prior Publication Data

US 2021/0127949 A1 May 6, 2021

Related U.S. Application Data (60) Provisional application No. 62/928,854, filed on Oct. 31, 2019.

(51) Int. Cl.
*A61B 1/00* (2006.01)
*A61B 1/018* (2006.01)
(Continued)

(52) U.S. Cl.
CPC ...... *A61B 1/00055* (2013.01); *A61B 1/00009* (2013.01); *A61B 1/00042* (2022.02); *A61B 1/0005* (2013.01); *A61B 1/00097* (2022.02); *A61B 1/00147* (2013.01); *A61B 1/018* (2013.01); *A61B 1/05* (2013.01); *A61B 1/267* (2013.01); *A61B 90/36* (2016.02); *A61B 2090/368* (2016.02)

(58) Field of Classification Search
CPC ....... A61B 1/267; A61B 1/05; A61B 1/00002; A61B 1/00004; A61B 1/00009; A61B 1/04; A61B 1/042; A61B 1/00105; A61B 1/00108; A61B 1/00039–00042; A61B 1/00045–00052
See application file for complete search history.

(56) References Cited

U.S. PATENT DOCUMENTS

| 5,529,570 A | 6/1996 | Storz |
| 7,568,619 B2 | 8/2009 | Todd et al. |

(Continued)

FOREIGN PATENT DOCUMENTS

| EP | 2433553 A1 | 3/2012 |
| JP | 2014210085 A | 11/2014 |

(Continued)

OTHER PUBLICATIONS

Ambu_aScope_3_Large_Brochure_4963605 (Oct. 2017).
(Continued)

*Primary Examiner* — Alexandra L Newton (57) ABSTRACT

An endoscope system is provided with a graphical orientation indicator. An endoscope includes a flexible tubular body with a steerable distal end having a camera. A controller for the endoscope presents a user interface that displays a view from the camera and a graphical orientation indicator visually representing an orientation of the distal end of the endoscope.

20 Claims, 7 Drawing Sheets

(51) Int. Cl.
*A61B 1/05* (2006.01)
*A61B 1/267* (2006.01)
*A61B 90/00* (2016.01)

(56) References Cited

U.S. PATENT DOCUMENTS

| | | | |
|---|---|---|---|
| 8,055,830 | B2 | 11/2011 | Waldhoff et al. |
| 8,194,122 | B2 | 6/2012 | Amling et al. |
| 8,634,031 | B2 | 1/2014 | Ikeda |
| 8,652,033 | B2 | 2/2014 | Berci et al. |
| 8,715,172 | B1 | 5/2014 | Girgis |
| 8,746,239 | B2 | 6/2014 | Yoshida |
| 8,827,899 | B2 | 9/2014 | Farr et al. |
| 8,982,199 | B2 | 3/2015 | Amling et al. |
| 9,033,895 | B2 | 5/2015 | Furlong et al. |
| 9,498,112 | B1 | 11/2016 | Stewart et al. |
| 9,538,908 | B2 | 1/2017 | Allyn et al. |
| 9,687,141 | B2 | 6/2017 | McGrath |
| 9,820,641 | B2 | 11/2017 | McGrath |
| 10,149,957 | B2 | 12/2018 | Runnels |
| 11,511,064 | B2 * | 11/2022 | Taniguchi ............... A61B 1/267 |
| 2005/0272971 | A1 * | 12/2005 | Ohnishi ............... A61B 1/0005 600/101 |
| 2006/0084840 | A1 * | 4/2006 | Hoeg ..................... A61B 1/042 600/117 |
| 2006/0247606 | A1 | 11/2006 | Batch |
| 2007/0167686 | A1 | 7/2007 | McGrath |
| 2007/0197896 | A1 | 8/2007 | Moll et al. |
| 2008/0177146 | A1 | 7/2008 | Chen |
| 2008/0177148 | A1 | 7/2008 | Chen et al. |
| 2008/0312507 | A1 | 12/2008 | Kim |
| 2009/0187078 | A1 | 7/2009 | Dunlop |
| 2010/0125166 | A1 * | 5/2010 | Henzler ............. G02B 23/2484 600/109 |
| 2011/0130632 | A1 | 6/2011 | McGrail et al. |
| 2011/0137127 | A1 | 6/2011 | Schwartz |
| 2011/0245609 | A1 | 10/2011 | Laser |
| 2013/0204085 | A1 | 8/2013 | Alexander et al. |
| 2013/0237763 | A1 | 9/2013 | Qui |
| 2014/0160261 | A1 | 6/2014 | Miller et al. |
| 2014/0266577 | A1 | 9/2014 | Anderson et al. |
| 2015/0080655 | A1 | 3/2015 | Peterson et al. |
| 2016/0120394 | A1 | 5/2016 | McGrath et al. |
| 2016/0279365 | A1 | 9/2016 | Esnouf |
| 2017/0215720 | A1 | 8/2017 | Walker et al. |
| 2019/0133430 | A1 | 5/2019 | Inglis et al. |
| 2019/0142262 | A1 | 5/2019 | Inglis et al. |
| 2019/0159662 | A1 * | 5/2019 | Papas .................. A61B 1/00032 |
| 2019/0246873 | A1 * | 8/2019 | Lu ...................... A61B 1/00105 |
| 2020/0254204 | A1 | 8/2020 | Moffat et al. |

FOREIGN PATENT DOCUMENTS

| | | |
|---|---|---|
| WO | 2011141686 A1 | 11/2011 |
| WO | 2018005842 A1 | 1/2018 |
| WO | 2018136905 A1 | 7/2018 |
| WO | 2022/133248 A1 | 6/2022 |
| WO | 2022/266500 A1 | 12/2022 |

OTHER PUBLICATIONS

International Search Report and Written Opinion for PCT Application PCT/GB2018/053300 dated Feb. 20, 2019; 15 pgs.

International Search Report and Written Opinion for PCT/US2020/051734 dated May 14, 2020; 11 pgs.

Rothfield, Kenneth; "The video laryngoscopy market: Past, present, and future," Anesthesiology News Guide to Airway Management, 2014, pp. 29-34.

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Höller, Kurt et al., "Endoscopic Orientation Correction," Big Data Analytics in the Social and Ubiquitous Context: 5th International Workshop on Modeling Social Media, MSM 2014, 5th International Workshop on Mining Ubiquitous and Social Environments, Muse 2014 and First International Workshop on Machine Le, Sep. 20, 2009, 8 pgs.

International Search Report and Written Opinion for PCT Application No. PCT/EP2020/080489, mailed Feb. 17, 2021, 12 pgs.

Lee, Hyung-Chul et al.; "Real-time endoscopic image orientation correction system using an accelerometer and gyrosensor," PLOS ONE, 12(11), Nov. 3, 2017, 12 pgs.

* cited by examiner

USER INTERFACE FOR STEERABLE ENDOSCOPE

CROSS-REFERENCE TO RELATED APPLICATIONS

The present application claims priority to and the benefit of U.S. Provisional Application No. 62/928,854, filed on Oct. 31, 2020, the disclosure of which is incorporated by reference in their entirety for all purposes.

BACKGROUND

The present disclosure relates generally to medical devices and, more particularly, to steerable introducers, such as a flexible endoscope, with graphical, e.g., displayed, orientation indicators, and related methods and systems.

Medical endoscopes are long, flexible instruments that can be introduced into a cavity of a patient during a medical procedure in a variety of situations to facilitate visualization and/or medical procedures within the cavity. For example, one type of scope is an endoscope with a camera at its distal end. The endoscope can be inserted into a patient's mouth, throat, or other cavity to help visualize anatomical structures, or to facilitate procedures such as biopsies or ablations. The endoscope may include a steerable distal tip that can be actively controlled to bend or turn the distal tip in a desired direction, to obtain a desired view or to navigate through anatomy. However, these steerable scopes can be difficult to maneuver into the desired location and orientation within a patient's anatomy.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, an endoscope system includes an endoscope having a steerable distal end with a camera and an orientation sensor. The endoscope system also includes a hand-held controller in communication with the endoscope. The hand-held controller includes a display screen and a hardware memory. The hardware memory stores instructions for displaying on the display screen a view from the camera and a graphical orientation indicator representing an orientation of the steerable distal end of the endoscope; detecting rotational movement of the steerable distal end of the endoscope; maintaining a rotational orientation of the view from the camera displayed on the display screen; and modifying the graphical orientation indicator to represent the detected rotational movement of the steerable distal end.

In another embodiment, an endoscope system includes an endoscope having a steerable distal end with a camera and an orientation sensor. The endoscope system also includes a controller in communication with the endoscope and including a display screen. The endoscope system also includes a user interface (UI) presented on the display screen. The UI includes a window displaying a view from the camera; an orientation icon visually representing a first orientation of the steerable distal end; and a touch interface for receiving a touch input from a user. The controller includes a hardware memory storing instructions for detecting a change to a second orientation of the steerable distal end of the endoscope, and modifying the orientation icon to visually represent the second orientation.

In another embodiment, method for operating a UI for an endoscope system includes the steps of displaying, on a touch screen display, a view from an endoscope and a graphical orientation indicator, the endoscope comprising a steerable distal end with a camera; receiving, via the touch screen display, a user input to steer the distal end of the endoscope; in response to the user input, steering the endoscope to a changed orientation of the distal end; and modifying the graphical orientation indicator to visually represent the changed orientation of the distal end.

Features in one aspect or embodiment may be applied as features in any other aspect or embodiment, in any appropriate combination. For example, any one of system, laryngoscope, handle, controller, endoscope, or method features may be applied as any one or more other of system, laryngoscope, controller, endoscope, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A medical scope or endoscope as provided herein is a thin, elongated, flexible instrument that can be inserted into a body cavity for exploration, imaging, biopsy, or other clinical treatments, including catheters, narrow tubular instruments, or other types of scopes or probes. Endoscopes may be navigated into the body cavity (such as a patient's airway, gastrointestinal tract, oral or nasal cavity, or other cavities or openings) and be steered by the user via advancement of the distal end to a desired position and, in certain embodiments, biomimetic motion of the endoscope. Endoscopes may be tubular in shape.

Advancement of long, flexible medical devices into patient cavities is typically via force transferred from a proximal portion of the device (outside of the patient cavity), that results in advancement of the distal tip within the patient cavity. For example, a doctor or other caregiver holding a proximal portion (such as a handle) of the medical device outside of the patient cavity pushes downward or forward, and the resulting motion is transferred to the distal tip, causing the tip to move forward within the cavity. Similarly, a pulling force applied by the caregiver at the proximal portion may result in retreat of the distal tip or movement in an opposing direction out of the patient cavity. However, because patient cavities are not regularly shaped or sized, the endoscope moves through a tortuous path, and the transferred force in a pushing or pulling motion from the proximal end may not result in predictable motion at the distal tip. Further, navigation of the endoscope through a curved passage may involve multiple rotations or turns of the distal and, and it can be difficult for the user to keep track of the changed orientation of the distal tip during and after the navigation. Subsequently, the user may inadvertently bend or turn the endoscope in the wrong direction. For example, a user may intend to steer the endoscope to the user's right, but because the endoscope is rotated from its default position, the result of this command is for the endoscope to bend to the user's left. As a result, it can be difficult for the user to anticipate how the endoscope will respond to steering instructions during a medical procedure.

Provided herein is a graphic user interface (UI) for a steerable endoscope, with one or more graphical orientation indicators that indicate a current orientation or articulation of the endoscope. According to an embodiment, an endoscope system includes an endoscope with a steerable distal end and a camera, and a control wand with a display screen and user input (such as a touch screen). The display screen displays the view from the camera, along with graphical indicators that show how the endoscope has been turned or rotated, to help the user manipulate the endoscope during medical procedures.

Figure 1:
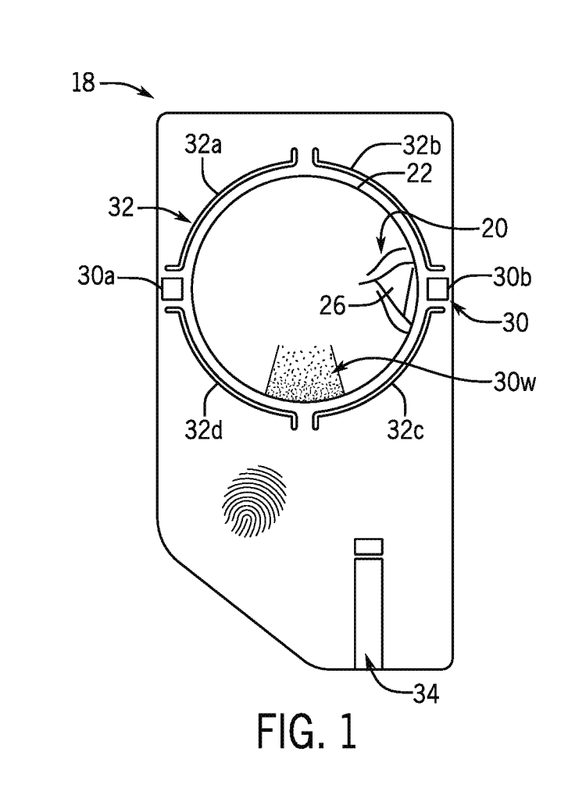
FIG. 1 is a front view of a user interface (UI) for an endoscope system, according to embodiments of the present disclosure.

An endoscope system 100 according to an embodiment is shown in FIGS. 1-2. The system includes an endoscope 12 and a controller 14 with a display screen 16. The endoscope 12 includes a steerable distal end 24 that carries a camera and an orientation sensor. The controller 14 is coupled to the endoscope 12 to provide power and/or control instructions to the steerable endoscope 12 and to receive data from the camera and the orientation sensor. In this embodiment, the controller 14 is implemented as a video laryngoscope.

A user interface (UI) 18, e.g., a graphical UI (GUI), is presented on the display screen 16. The UI 18 includes a view 20 from the endoscope (such as a video feed or still image from the endoscope camera), a touch screen interface, and three graphical orientation indicators 30, 32, 34. The endoscope view 20 is presented in a circular shape, inside a circular outline 22. In the example shown, the view is pointed at the user's vocal cords and trachea 26. FIGS. 2A-E include five different presentations of the UI 18, in five views A, B, C, D, and E. This figure also shows the endoscope 12 connecting to the laryngoscope 14, such as by connecting the proximal end of the endoscope 12 to a port on the back of the laryngoscope screen 16. The opposite distal end 24 of the endoscope is inserted into the patient. The distal end 24 is actively steerable and includes a camera and an orientation sensor, as described below.

It should be understood that the disclosed techniques may support visualization and navigation of orientation for a blind steerable introducer, i.e., an elongated flexible instrument that does not include a camera or for which the camera is not activated.

The three orientation indicators 30, 32, 34 are shown in a close-up view of the UI 18 in FIG. 1. The orientation indicator 30 is a roll indicator, which graphically depicts the current roll orientation of the distal end 24 of the endoscope 12. In the embodiment of FIG. 1, the roll indicator 30 includes a horizon indicator represented by two markers 30a, 30b placed 180 degrees apart on or near the circular outline 22. The markers 30a, 30b are shown as small solid squares, but can be other shapes and sizes. For example, in another embodiment, the horizon indicator is a dashed line that is shown across the view 20 from marker 30a to marker 30b. When the markers 30a, 30b are horizontal on the screen, the distal end 24 is in its default or resting position, meaning it has not been actively steered to rotate.

Figure 2A:
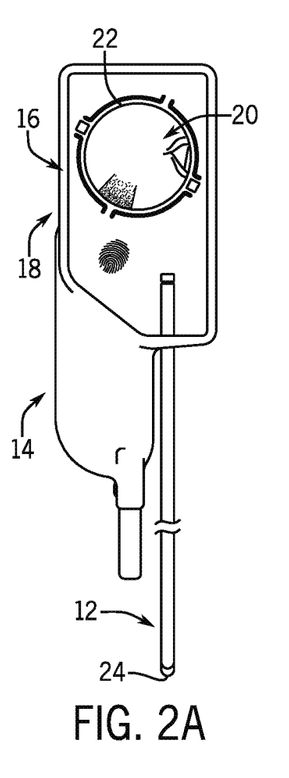
FIG. 2A is a view of an endoscope system including the UI of FIG. 1, according to embodiments of the present disclosure.
Figure 2B:
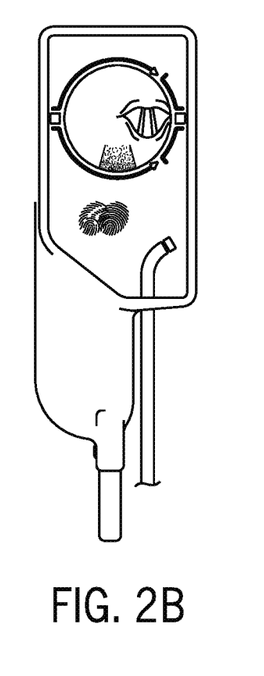
FIG. 2B is a view of an endoscope system including the UI of FIG. 1, according to embodiments of the present disclosure.
Figure 2C:
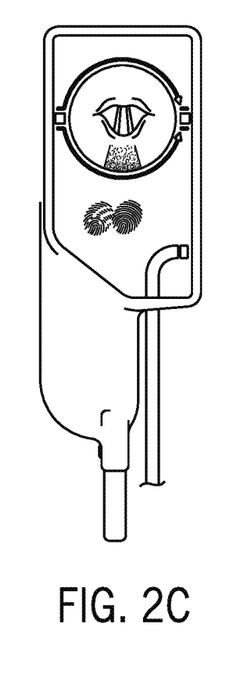
FIG. 2C is a view of an endoscope system including the UI of FIG. 1, according to embodiments of the present disclosure.
Figure 2D:
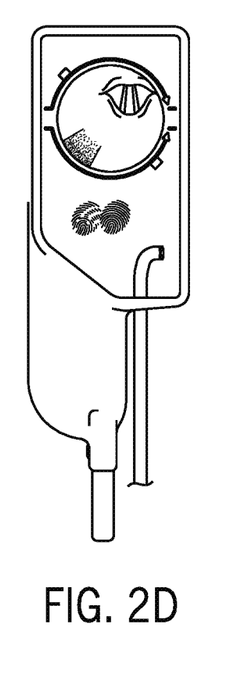
FIG. 2D is a view of an endoscope system including the UI of FIG. 1, according to embodiments of the present disclosure.
Figure 2E:
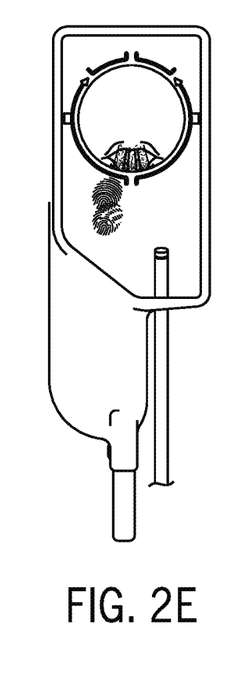
FIG. 2E is a view of an endoscope system including the UI of FIG. 1, according to embodiments of the present disclosure.

The roll indicator 30 moves when the distal end 24 of the endoscope rotates within the patient cavity. This rolling movement is shown in views A and D of FIG. 2. In views A and D, the distal end 24 has rotated clockwise about 20 degrees compared to its default position. To indicate this rotation, the markers 30a, 30b have been moved proportionately, about 20 degrees, around the image view 20. Notably, in FIG. 2, the image view 20 itself has not rotated. In this embodiment, the endoscope system includes an image correction or adjustment feature that counter-rotates the image to keep the image upright (with the posterior direction of the patient, toward the patient's chest, maintained in the "up" direction on the screen 16), even when the endoscope is actively steered and rotated. This type of image adjustment can be accomplished by counter-rotating the image proportionately based on an amount of rotation detected by the orientation sensor at the distal end of the endoscope, as more fully described in Applicant's U.S. Provisional App. No. 62/812,678, filed Mar. 1, 2019, and U.S. patent application Ser. No. 16/802,242, published as U.S. Patent Publication No. 20200275824, the entire contents of which are hereby incorporated by reference.

Referring again to the views of FIG. 2, the user can actively steer the endoscope, such as rotating the distal end 24, while the image is kept stable in the image view 20. In this case, the user could lose track of the steering inputs that have been given to the endoscope, and could have difficulty remembering how the endoscope is currently rotated or positioned within the patient cavity. The roll indicator 30 provides the user with a visible graphic representation of the current rotational orientation of the endoscope, so that the user can easily keep track of that orientation.

In FIGS. 1 and 2A-E, the roll indicator 30 also includes a working channel indicator 30W. The working channel indicator is a shown as a transparent shaded region overlaid onto the image 20. This indicator shows the rotational location of a working channel on the endoscope 12. A working channel can be an open lumen formed longitudinally in the endoscope to allow for the passage of tools or fluids, such as biopsy tools, atomizing catheters, saline, and fluids to be evacuated from the body. The working channel may be formed off-set from the center axis of the endoscope, in which case it will move rotationally when the endoscope is rotated. The indicator 30W visually represents on the UI 18 where the working channel is currently located, so that the user can anticipate where a tool, fluid, or other instrument will enter the image 20 when it emerges from the working channel. If the working channel is not aligned with the anatomical area that it needs to access (for a particular clinical procedure), the user can steer the endoscope to move the working channel into the desired position.

A second orientation indicator 32 is a pitch/yaw indicator, which indicates the amount and direction that the endoscope has been curved, bent, or turned. In the embodiment shown, the pitch/yaw indicator 32 is depicted by bracket lines 32*a*, 32*b*, 32*c*, and 32*d* formed around the outline 22 of the image 20. When the endoscope is turned left or right (yaw) or up or down (pitch), the bracket lines grow and shrink, as shown in FIG. 2 in views B, C, D, and E. In view B, the distal end 24 has been turned to the right, and the brackets 32*a* and 32*d* have grown bigger, while brackets 32*b* and 32*c* have been made smaller, to show that the endoscope has turned to the right. The lines that grew (32*a*, 32*d*) also have arrows on the end in the direction that the endoscope turned. In view B, the endoscope has turned to the right part of the way through its range of motion. In view C, the endoscope has turned all the way to the limit of its range of motion, and thus the lines 32*a*, 32*d* have come all the way around the image view 20, and lines 32*b*, 32*c* are removed entirely or shown only as small dashed lines or markers. With these changes, the yaw/pitch indicator 32 shows the user which direction the endoscope has turned, and how far within its range of motion. The user can then appreciate, by viewing the UI 18, how the endoscope is turned or bent, and how much further it can still turn from there.

Pitch is indicated in view E of FIG. 2. In this view, lines 32*c*, 32*d* on the bottom side of the image view 20 have grown, and lines 32*a*, 32*b* on the top have shrunk, so that the lines show the user that the endoscope is bent upward. The lines 32*c*, 32*d* have arrows pointing upward in that same direction, toward the top of the screen, to further reiterate the direction that the endoscope is turned.

A third orientation indicator 34 is a graphical representation of the distal end 24 of the endoscope 12. For example, this indicator 34 can be a cartoon graphic or icon representing an endoscope tip end. As shown in views A-E of FIG. 2, the icon curves and turns in coordination with the distal end 24 of the endoscope. This indicator 34 provides another way to visually represent on the screen 16 the current orientation of the endoscope.

Views A, B, C, D, and E in FIG. 2 show the UI 18 in various states based on active movement of the endoscope 12. In view A, the endoscope has been rotated about 20 degrees clockwise, as shown by the clockwise rotation of the roll indicator 30 (markers 30*a*, 30*b*, and working channel indicator 30W). In view B, the endoscope is rolled back to neutral, and turns partway to the right, as shown by the indicators 32 (the bracket lines) and 34 (the tip icon). The thumb-prints in view B show an example of a user input to steer the endoscope to turn it to the right; in this case, the user taps or drags/swipes a thumb to the right to instruct the endoscope to bend to the right. In view C, the user taps or drags/swipes further to the right (as shown by the thumb-prints), to instruct the endoscope to continue to bend to the right. In this example, in view C the endoscope reaches the limit of its range of motion to the right. In view D, the endoscope is rolled to the right (clockwise). In an embodiment, rotational movement of the endoscope is accomplished by the user manually twisting the endoscope. In view E, the endoscope pitches upward, based on a user input to move the view upward (such as moving the thumb up as shown by the thumbprints in view E). Although these views are shown as snapshots, the indicators 30, 32, 34 are dynamic and change in real-time along with the position of the distal end 24. The indicators may be moved between discrete configurations, or may continually change shapes, colors, or forms, or may be animated.

Orientation indicators may be presented within the clinical view from the endoscope camera, outside of the clinical view on the display screen, or overlapping both the clinical view and other areas of the screen. Another endoscope system 300 according to an embodiment is shown in FIGS. 3A-D. In this embodiment shown in FIG. 3D, an endoscope 312 connects to a video laryngoscope 314 with a display screen 316. A graphical user interface (UI) 318 is presented on the display screen. The UI 318 includes two orientation indicators 330, 336. The first orientation indicator 330 includes a roll indicator, which indicates a rotational position of the distal end 324 of the endoscope 312. The roll indicator includes two triangular horizon indicators 330*a*, 330*b* and a working channel indicator 330W. In this embodiment, the working channel indicator 330W overlaps the circular outline 322 of the camera view 320, crossing over the circular outline. The working channel indicator 330W is shown as two lines approximately perpendicular to the circular outline, partially internal and partially external to the circular camera view 320. The indicators 330*a*, 330*b*, 330W move around the circle 322 in synchrony with the orientation of the distal end 324 of the endoscope 312. For example, in view A of FIG. 3, the endoscope has been rotated about 45 degrees clockwise, and the indicators 330*a*, 330*b*, and 330W have been rotated around the circle a corresponding amount.

Figure 3A:
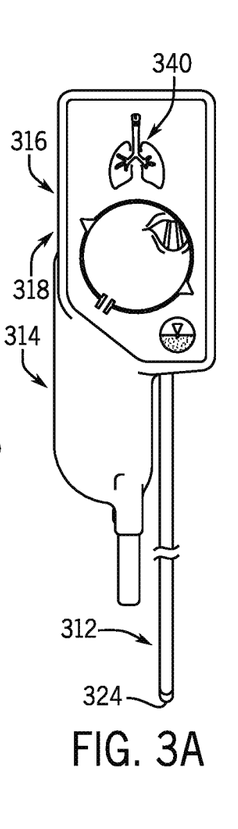
FIG. 3A is a view of an endoscope system and UI, according to embodiments of the present disclosure.
Figure 3B:
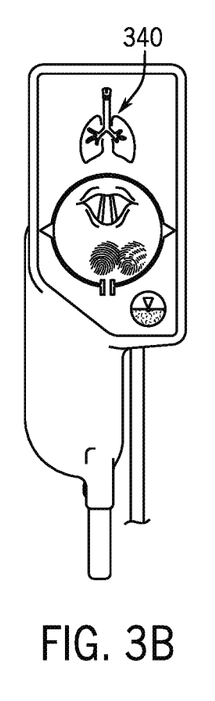
FIG. 3B is a view of an endoscope system and UI, according to embodiments of the present disclosure.
Figure 3C:
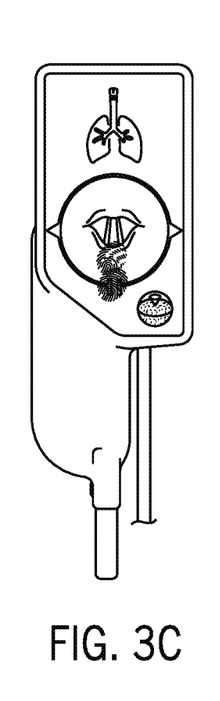
FIG. 3C is a view of an endoscope system and UI, according to embodiments of the present disclosure.
Figure 3D:
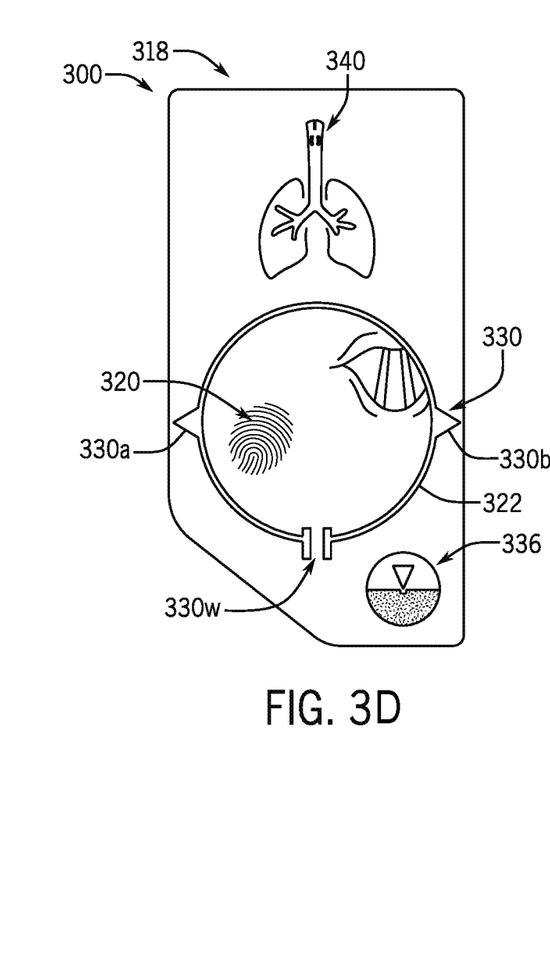
FIG. 3D is a view of an endoscope system and UI, according to embodiments of the present disclosure.

A second graphical indicator 336 includes a gravity indicator, which indicates the orientation of the distal tip 324 relative to gravity. The gravity indicator can be presented in various styles or shapes. In this embodiment, it is shown as a pin or marker with a tip pointed down toward the bottom of the screen 316. The pin is inside a circle with a line or plane that indicates a level horizon. The view of this pin changes when the endoscope tip pitches up or down. As shown in view C in FIG. 3, the gravity marker tilts to indicate that the endoscope tip 324 has pitched up. When the tip 324 pitches up, the plane of the pin also tilts up. When the endoscope is neutral (not pitched up or down), the gravity indicator is level, as shown in views A and B.

Figure 4:
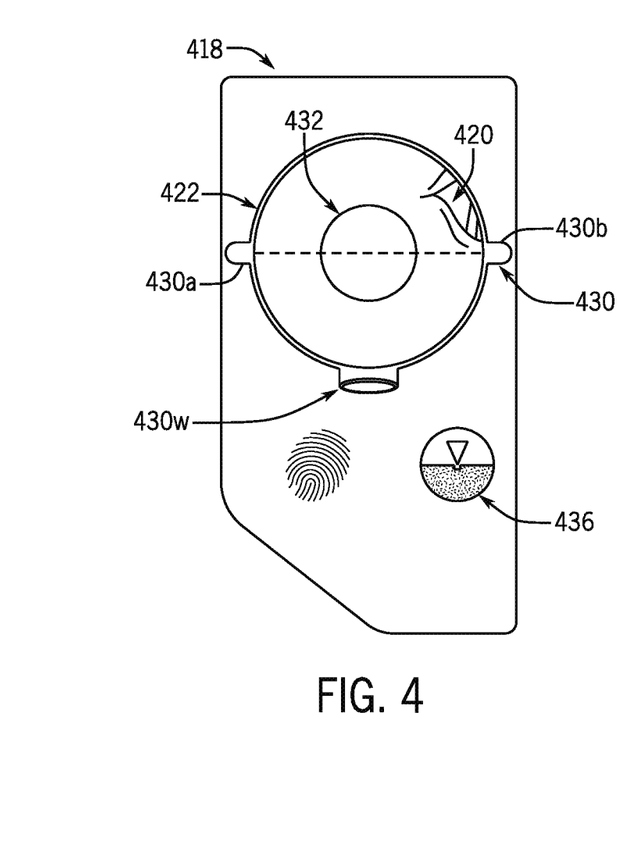
FIG. 4 is a front view of a UI for an endoscope system, according to embodiments of the present disclosure.

The UI 318 also includes a status indicator or icon 340, above the camera view 320. In the embodiment shown, the status indicator 340 is a lung icon. This area of the UI may be used to indicate what type of procedure is being performed, or other types of status information, such as a distance from the vocal cords or distance from user-defined waypoints. The UI embodiments disclosed herein may be displayed on a controller that is in communication with the endoscope. The controller may be a hand-held device with a screen, such as a video laryngoscope, a wand, puck, tablet, or other type of display screen. FIGS. 4-5 show an embodiment in which the controller is implemented as a hand-held wand. An endoscope system 400 includes an endoscope 412 connected to a hand-held wand 413 with a display screen 416. A UI 418 is presented on the screen 416. In this embodiment, the UI 418 includes a roll indicator 430 (including two horizon markers 430a, 430b spaced 180 degrees apart, a dashed horizon line between them, and a working channel indicator 430W). As shown in view A of FIG. 5, the roll indicator 430 rotates on the UI 418 to indicate the degree and direction of rotation of the distal end 424 of the endoscope 412. As discussed above, when the endoscope rotates, in an embodiment, the view from the endoscope camera is adjusted on the screen 416, to keep the direction of gravity pointed down toward the bottom of the screen 416. Thus, in view A, the roll indicator 430 rotates but the image 420 does not.

Figure 5A:
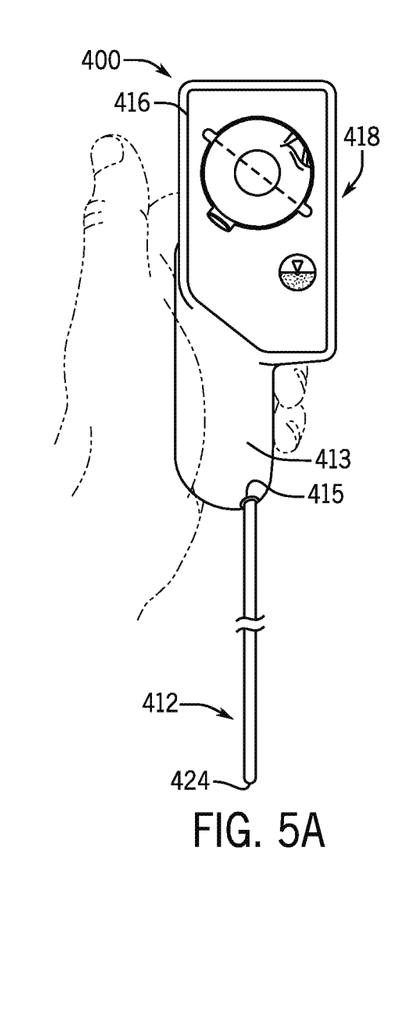
FIG. 5A is a view of an endoscope system including the UI of FIG. 4, according to embodiments of the present disclosure.
Figure 5B:
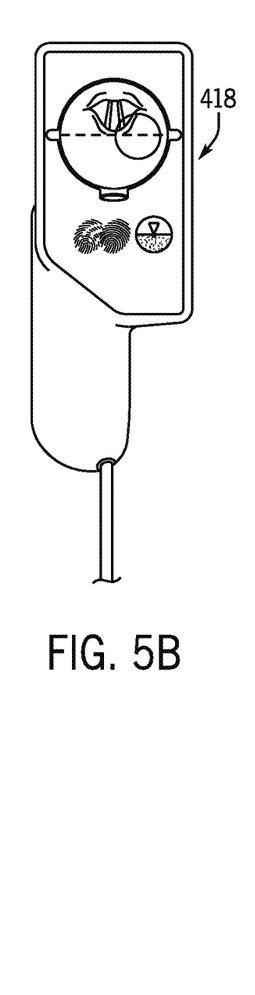
FIG. 5B is a view of an endoscope system including the UI of FIG. 4, according to embodiments of the present disclosure.
Figure 5C:
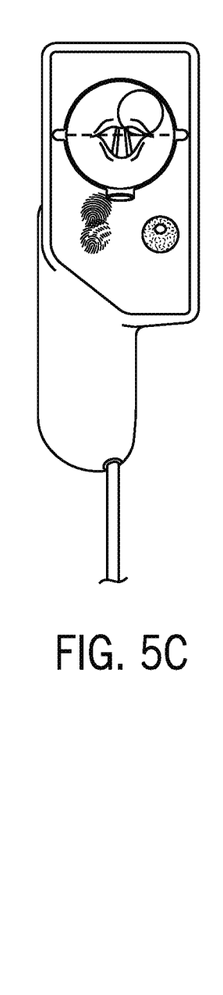
FIG. 5C is a view of an endoscope system including the UI of FIG. 4, according to embodiments of the present disclosure.
Figure 5D:
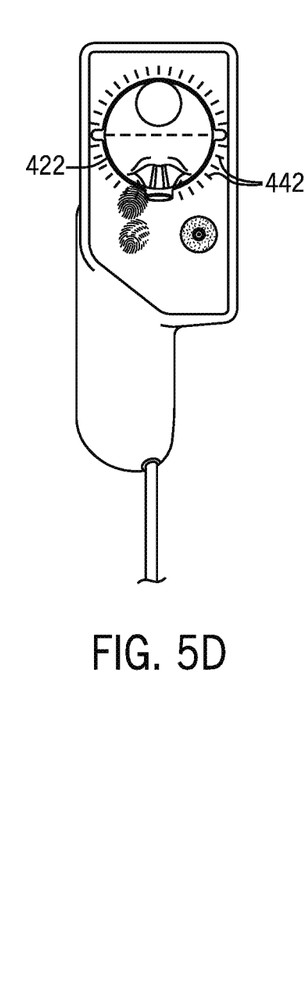
FIG. 5D is a view of an endoscope system including the UI of FIG. 4, according to embodiments of the present disclosure.
Figure 5E:
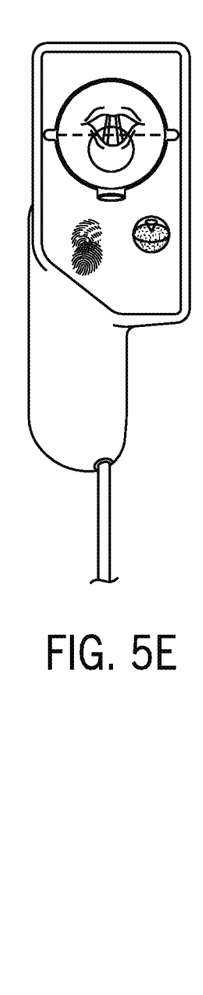
FIG. 5E is a view of an endoscope system including the UI of FIG. 4, according to embodiments of the present disclosure.

The UI 418 also includes a pitch/yaw indicator 432, in this case implemented as a crosshairs or bubble 440. The bubble 440 shows the direction of yaw (left or right) or pitch (up or down) movement of the endoscope 412. In view B, the user steers the endoscope to the right (as indicated by the thumb prints tapping to the right on the touch screen), and the bubble 440 also moves to the right within the camera viewing window 420 on the screen. In view C, the user steers the endoscope to pitch up, and the bubble 440 moves up. In an embodiment, distance that the bubble 440 moves within the window 420 corresponds to the amount that the endoscope has turned. In an embodiment, the bubble 440 reaches the circular outline 422 when the endoscope reaches its limit of motion. This is depicted in view D of FIG. 5, where the endoscope has pitched up (bent upward) as far as it can go, and the bubble 440 comes into contact with the top edge of the circle 422. In an embodiment, the UI 418 also provides an additional limit indicator, such as rays 442, when a limit of motion of the endoscope is reached. The rays 442 appear around the circle view 420 when the endoscope reaches its limit of motion, and then the rays 442 disappear when the endoscope moves back in the other direction, away from the respective limit. The controller 414 may also provide a haptic response when a limit of motion is reached, such as providing a short pulse, buzz, or vibration from a haptic generator. The haptic feedback may be proportional to the size of the signal, with a larger feedback associated with movements at or past a range of motion of the endoscope.

As shown in FIGS. 4-5, the UI 418 also includes a gravity indicator 436, which indicates the direction of gravity relative to the endoscope orientation. When the endoscope is level with gravity (not pitched up or down), the gravity indicator 436 shows a level line below the pointed pin. When the endoscope tip pitches up (as in view C), the gravity indicator also pitches, so that the view moves up over the pointed pin. When the endoscope tip reaches its upward limit of motion (as in view D), the gravity indicator has moved all the way to the top, above the pointed pin, to indicate that the direction of gravity is directly below the view 420 from the endoscope. This is just one way to indicate the direction of gravity relative to the tip, and other gravity indicators may be used.

In FIGS. 4-5, the controller is a hand-held wand 413, rather than a video laryngoscope (shown in other figures). The endoscope 412 connects directly to the wand 413, such as by plugging the proximal end of the endoscope 412 into a port 415 on the wand 413, for passage of control signals from the wand to the endoscope and video signals from the endoscope to the wand. In an embodiment, the endoscope 412 is removable from the wand 413. The endoscope 412 may be single-use only and discarded (or recycled) after use, and the controller (such as wand 413) may be re-usable. In other embodiments the controller may have other forms or structures. For example, the controller may be a video laryngoscope, table-top display screen, tablet, laptop, puck, or other form factor. The controller with the endoscope operates as a two-part endoscope, where the controller serves as the handle, display, and user input for the endoscope. In an embodiment, the controller is reusable and the endoscope is single-use and disposable, to prevent cross-contamination between patients or caregivers. The controller itself does not need to come into contact with the patient, and it can be wiped and cleaned and ready to use for the next patient, with a new sterile endoscope.

Figure 6:
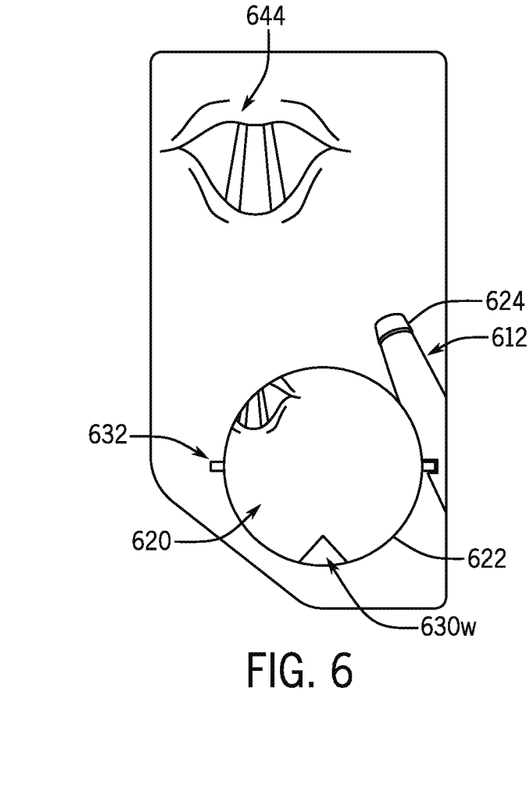
FIG. 6 is a front view of a UI for an endoscope system, according to embodiments of the present disclosure.

An embodiment in which the controller is implemented as a video laryngoscope is shown in FIGS. 6-7. In this embodiment, two image views are displayed on the display screen at the same time, one from a camera of the video laryngoscope, and one from a camera of the endoscope. As shown in the figures, an endoscope system 600 includes an endoscope 612 connected to a video laryngoscope 614 with a display screen 616. The display screen presents a UI 618, which displays a first view 644 from the video laryngoscope camera and a second view 620 from the endoscope camera. These two image views are displayed at the same time on the UI, such as with one image overlapping the other. In an embodiment, the video laryngoscope image 644 is shown within a first outline shape (such as a rectangular corner or outline), and the endoscope image 620 is shown within a second different outline shape (such as a circular corner or outline 622), to help differentiate the two images. In FIG. 6, the distal end 624 of the endoscope 612 is visible in the first image view 644 from the video laryngoscope camera.

The UI 618 includes a roll indicator 630, and a pitch/yaw indicator 632. The roll indicator 630 may be located on the circle 622 to correspond to the location of a working channel of the endoscope. As shown in views A, B, C, and D of FIG. 7, the roll indicator 630 rotates to indicate roll of the distal end 624, and the pitch/yaw indicator lines 632 move around the outline 622 to indicate left/right yaw or up/down pitch of the distal end 624. In view A, the user uses the right hand to twist or rotate the endoscope to the left (counter-clockwise), and the roll indicator 630 moves a corresponding amount along the circle 622. The user can see the movement of the distal end 624 within the video laryngoscope image 644. In view B, the user instructs the endoscope to yaw to the left, such as by tapping with the thumb of the left hand in the left direction on the screen 616. The yaw/pitch indicator lines 632 move around the circle toward the left, to indicate the change in position of the endoscope. The video laryngoscope image 644 shows the distal end 624 curved to the left. In view C, the user instructs the endoscope to pitch upward, such as by tapping up on the screen. The yaw/pitch indicator lines 632 move up a corresponding amount, and the video laryngoscope image 644 shows the distal end 624 curved upward. In view D, the user advances the endoscope through the patient's vocal cords and into the trachea 626, and instructs the endoscope to pitch down, as indicated by the thumb taps on the screen and the yaw/pitch indicator 632. The endoscope image 620 now shows a view of the tracheal walls of the patient.

Figure 7A:
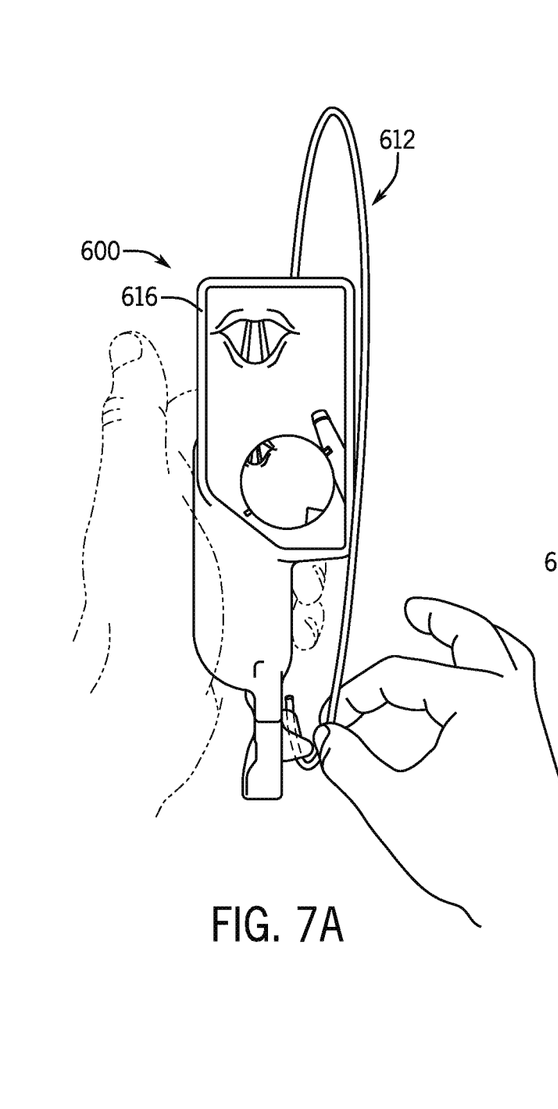
FIG. 7A is a view of an endoscope system and UI, according to embodiments of the present disclosure.
Figure 7B:
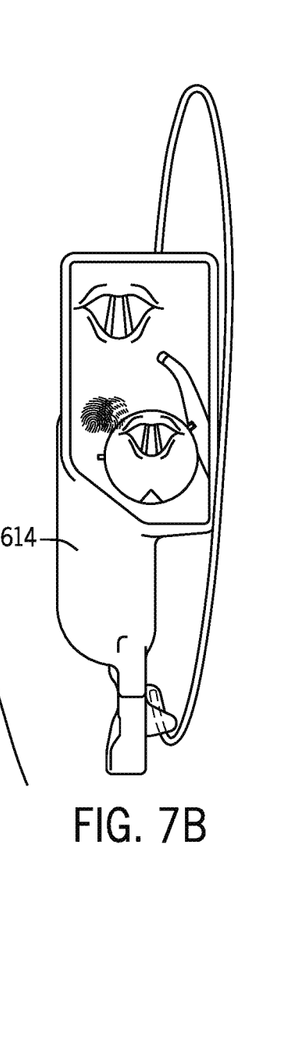
FIG. 7B is a view of an endoscope system and UI, according to embodiments of the present disclosure.
Figure 7C:
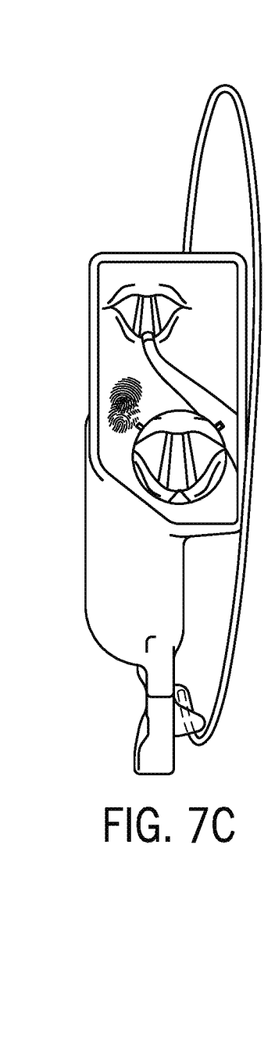
FIG. 7C is a view of an endoscope system and UI, according to embodiments of the present disclosure.
Figure 7D:
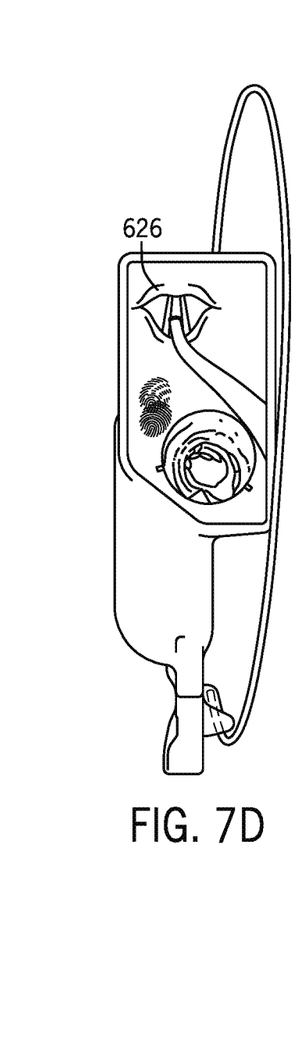
FIG. 7D is a view of an endoscope system and UI, according to embodiments of the present disclosure.

In an example use case, the endoscope system 600 is used to intubate a patient. With one hand (such as the left hand), the user holds the video laryngoscope 614 and taps on the screen 616 to steer the endoscope 612, and with the other hand (such as the right hand), the user pushes the endoscope 612 forward into the patient cavity. When the endoscope is in place (for an intubation, the endoscope is passed through the patient's vocal cords into the trachea, as shown in view D), the proximal end of the endoscope 612 is disconnected from the laryngoscope 614 and an endotracheal tube is passed over the endoscope. Once the proximal end emerges from the endotracheal tube, the endoscope 612 can be reconnected to the laryngoscope 614. The endotracheal tube is then passed along the endoscope into the trachea, and then the endoscope 612 can be withdrawn from the patient, retracting it back through the tube and leaving the endotracheal tube in place.

The endoscope includes one or more steerable segments at the distal end, to actively bend, turn, or curve the distal end of the endoscope. In an embodiment, the steerable segment can bend and curve in three dimensions (not just in a single plane, such as up/down or right/left), curving to point in all directions, up to a limit of its range of motion. For example, in an embodiment each segment can bend up to 90 degrees in any direction, enabling it to move within a hemisphere having a radius equal to the segment's length. Each segment is manipulated by its own actuation system, including one or more actuators (such as sleeved pull-wires or other actuators described below), which moves to bend or un-bend the segment into or out of a curved shape. In an embodiment, the endoscope includes two steerable segments at the distal end of the endoscope. The two steerable segments are coupled to each other, and each segment can articulate independently of the other segment.

Each articulating segment at the distal end of the endoscope is manipulated by a steering system, which operates an actuator that is coupled to the segment to bend or straighten the segment. The steering system may include one or more memory metal components (e.g., memory wire, Nitinol wire) that changes shape based on electrical input, a piezoelectric actuators (such as the SQUIGGLE motor from New Scale Technologies, Victor NY), a retractable sheath (retractable to release a pre-formed curved component such as spring steel which regains its curved shape when released from the sheath), mechanical control wires (pull wires), hydraulic actuators, servo motors, or other means for bending, rotating, or turning the distal end or components at the distal end of the endoscope.

In an embodiment, the camera is located at the distal end or terminus of the distal-most segment of the endoscope, to provide the camera with a clear forward view into the patient anatomy. In an embodiment, the orientation sensor is also located at the distal end, just proximally of the camera. In an embodiment, the orientation sensor is adjacent the camera. In an embodiment, the orientation sensor is mounted on a flex circuit behind the camera. In an embodiment, the orientation sensor is mounted on the same flex circuit as the camera, though the orientation sensor and the camera need not be in communication on the shared flex circuit. In an embodiment, the orientation sensor has a size of between 1-2 mm in each dimension.

The orientation sensor is an electronic component that senses the orientation (such as orientation relative to gravity) and/or movement (acceleration) of the distal end of the endoscope. The orientation sensor contains a sensor or a combination of sensors to accomplish this, such as accelerometers, magnetometers, and gyroscopes. The orientation sensor may be an inertial measurement unit (IMU). The orientation sensor detects static orientation and dynamic movement of the distal tip of the endoscope and provides a signal indicating a change in the endoscope's orientation and/or a motion of the endoscope. The orientation sensor sends this signal to the controller. The orientation sensor is located inside the tubular housing of the endoscope. In an embodiment, the orientation sensor is located very close to the terminus of the distal end of the endoscope, such as behind the camera, to enable the orientation sensor to capture much of the full range of movement of the distal tip and camera. In an embodiment, the orientation sensor is placed at a distal end of the first steerable portion, remote from the proximal end of the steerable portion, to place the orientation sensor away from the fulcrum of movement.

Figure 8:
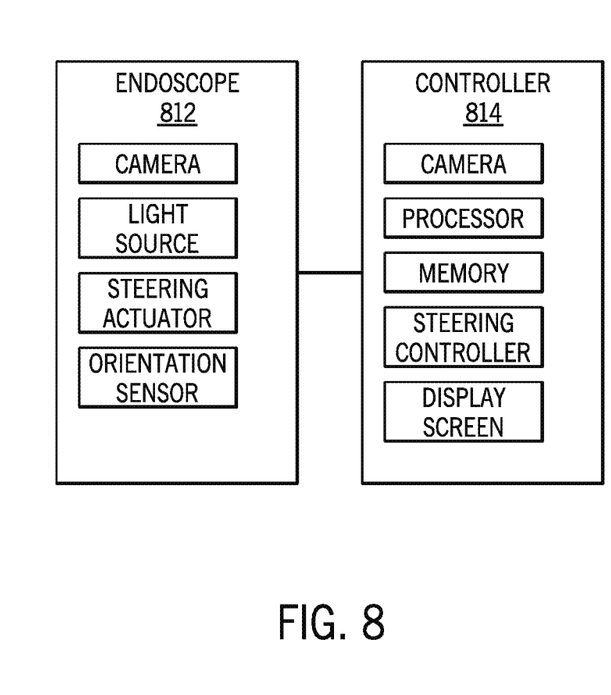
FIG. 8 is a block diagram of an endoscope system, according to embodiments of the present disclosure.

A block diagram of an endoscope system 800 is shown in FIG. 8, including an endoscope 812 and a controller 814. The connection between them may be wired (in which case they each have an electrical connector) or wireless (in which case they each include a wireless transceiver). The endoscope 812 includes a camera and an orientation sensor at the distal end of the endoscope. The orientation sensor may be an inertial measurement unit (IMU), accelerometer, gyroscope, or other suitable sensor. The endoscope 812 also includes a light source and an actuator that is coupled to the distal steerable segments, to bend or un-bend them, as described herein.

The controller 814 includes a processor or chip (such as a chip, a processing chip, a processing board, a chipset, a microprocessor, or similar devices), a hardware memory, a display screen (such as a touch screen), and a steering control system, which may include a motor or other driver for operating the actuator. The controller 814 may also include some other type of user input (buttons, switches), and a power source (such as an on-board removable and/or rechargeable battery).

The controller 814 may also include a power source (e.g., an integral or removable battery) that provides power to one or more components of the endoscope as well as communications circuitry to facilitate wired or wireless communication with other devices. In one embodiment, the communications circuitry may include a transceiver that facilitates handshake communications with remote medical devices or full-screen monitors. The communications circuitry may provide the received images to additional monitors in real time.

The processor may include one or more application specific integrated circuits (ASICs), one or more general purpose processors, one or more controllers, FPGA, GPU, TPU, one or more programmable circuits, or any combination thereof. For example, the processor may also include or refer to control circuitry for the display screen. The memory may include volatile memory, such as random access memory (RAM), and/or non-volatile memory, such as read-only memory (ROM). The image data may be stored in the memory, and/or may be directly provided to the processor. Further, the image data for each patient procedure may be stored and collected for later review. The memory may include stored instructions, code, logic, and/or algorithms that may be read and executed by the processor to perform the techniques disclosed herein.

Figure 9:
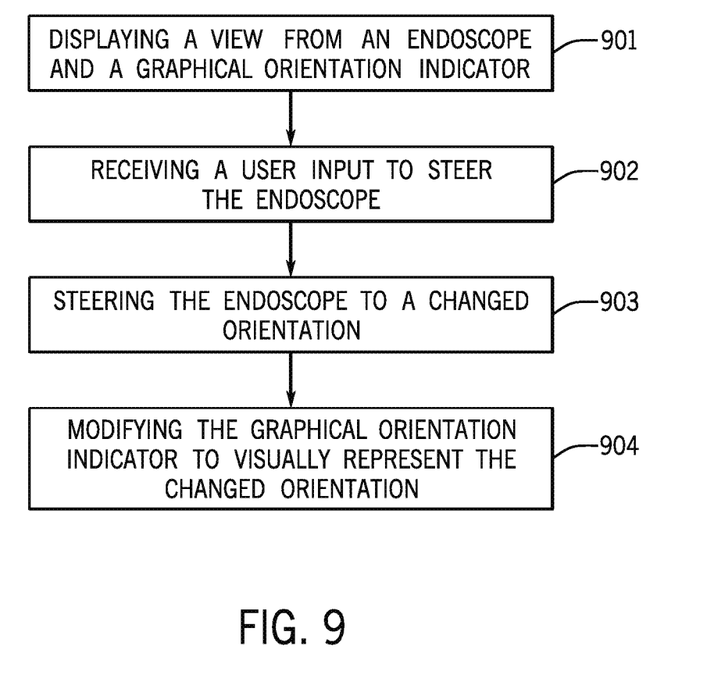
FIG. 9 is a flowchart of a method for use in conjunction with the UI for an endoscope system.

A method 900 for operating a UI for an endoscope system is shown in the flowchart of FIG. 9. The method includes displaying a view from an endoscope and a graphical orientation indicator, at 901. In an embodiment, the endoscope includes a steerable distal end with a camera, and the display is provided on a touch screen display. The method also includes receiving, via the touch screen display, a user input to steer the distal end of the endoscope, at 902. In response to the user input, the method includes steering the endoscope to a changed orientation of the distal end, at 903. The method includes modifying the graphical orientation indicator to visually represent the changed orientation of the distal end, at 904. In an embodiment, the graphical orientation indicator includes one or more of a roll, pitch, or yaw markers, and modifying it includes moving the markers around or along the camera view to represent the changed orientation of the distal end of the endoscope.

In an embodiment, the UI is implemented on a touch screen that is responsive to taps, touches, or proximity gestures from the user. The UI detects the user's touch and sends this touch input to a processor which generates instructions to operate the steering system to bend, turn, or move the endoscope. For example, the user may enter a touch gesture (such as a tap, double-tap, tap-and-hold, slide, or swipe) to identify a target point or direction within the image on the screen. This gesture identifies where the user desires to steer the endoscope, and the controller translates this into a real-world steering direction and corresponding instructions for operating the steering system to move the distal steerable segment of the endoscope in that direction. The user may swipe in a desired direction on the touch screen to reorient the distal end of the endoscope. A desired orientation or movement of the camera may be interpreted from the direction and length of the swipe movement on the touch screen. In one example, the direction of movement of the distal end of the endoscope is the same as the direction of the movement of user input. A swipe or slide to the right steers the endoscope to the right, bringing anatomical areas towards the right into view as the endoscope camera is steered right. Accordingly, in such an embodiment, left swipes steer left, upward swipes steer up, and downward swipes steer down. In another example, the direction of movement of the distal end of the endoscope is opposite the direction of the movement of user input. The steering operates in a manner similar to map or digital paper steering, and a swipe or slide to the right drags the entire image to the right and brings anatomical areas on the left into view as the endoscope camera is steered left. In this embodiment, left swipes steer right, upward swipes steer down, and downward swipes steer up.

In an embodiment, the steering input may additionally or alternatively be provided via user selection from a menu, selection of soft keys, pressing of buttons, operating of a joystick, etc. In an embodiment, the user holds the controller with a left hand and touches the screen with a thumb of the left hand, leaving the right hand free to hold, twist, and advance the endoscope. The user can steer the endoscope camera by tapping the screen with his or her thumb, and then can advance the endoscope by pushing it forward (or pulling back) with his or her right hand.

The steering response to the user input can correlate steering speed of the distal end of the endoscope to a speed of the user input. Thus, fast swiping motions result in faster movement of the distal end of the endoscope relative to slower swiping motions. A user can steer by selecting (tapping, swiping to) a portion of the displayed view from the endoscope as the steering destination. The steering speed towards the selection is correlated to the distance of the selected portion of the image from the distal end of the endoscope. For example, steering to a farther point, relative to the distal end, results in faster steering as compared to steering to a closer point.

While the present techniques are discussed in the context of endotracheal intubation, it should be understood that the disclosed techniques may also be useful in other types of airway management or clinical procedures. For example, the disclosed techniques may be used in conjunction with placement of other devices within the airway, secretion removal from an airway, arthroscopic surgery, bronchial visualization past the vocal cords (bronchoscopy), tube exchange, lung biopsy, nasal or nasotracheal intubation, etc. In certain embodiments, the disclosed visualization instruments may be used for visualization of anatomy (such as the pharynx, larynx, trachea, bronchial tubes, stomach, esophagus, upper and lower airway, ear-nose-throat, vocal cords), or biopsy of tumors, masses or tissues. The disclosed visualization instruments may also be used for or in conjunction with suctioning, drug delivery, ablation, or other treatments of visualized tissue and may also be used in conjunction with endoscopes, bougies, introducers, scopes, or probes.

The description and figures show a variety of icons, graphical indicators, lines, outlines, shading, markers, and visual indicators to represent a status or position of the endoscope. These different types of graphical indicators can be mixed and matched into various combinations, groups, and patterns. A shading or line pattern shown in connection with one indicator can be used with a different indicator, and so forth. Various combinations can be made to provide a desired indicator or animation.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. An endoscope system, comprising:
 an endoscope comprising a working channel and a steerable distal end with a camera and an orientation sensor; and
 a hand-held controller in communication with the endoscope and comprising a display screen and a hardware memory storing instructions for:
  displaying on the display screen:
   a view from the camera;
   a graphical orientation indicator representing an orientation of the steerable distal end of the endoscope; and
   a graphical working-channel indicator representative of a rotational orientation of the working channel of the endoscope;
  based on signals from the orientation sensor in the steerable distal end, detecting rotational movement of the steerable distal end of the endoscope;
  maintaining a rotational orientation of the view from the camera displayed on the display screen; and modifying the graphical orientation indicator and the working-channel indicator to represent the detected rotational movement of the steerable distal end.

2. The endoscope system of claim 1, wherein the graphical orientation indicator comprises a roll indicator, and wherein the stored instructions further comprise instructions for displaying a second graphical orientation indicator comprising a pitch or yaw indicator.

3. The endoscope system of claim 1, wherein the graphical orientation indicator comprises horizon markers.

4. The endoscope system of claim 1, wherein the view from the camera is displayed within a circle, and wherein the graphical orientation indicator comprises visual marks along the circle.

5. The endoscope system of claim 1, wherein the graphical orientation indicator comprises a gravity indicator.

6. The endoscope system of claim 1, wherein maintaining the rotational orientation of the view from the camera comprises counter-rotating the view in proportion to the detected rotational movement of the steerable distal end of the endoscope.

7. The endoscope system of claim 1, wherein the endoscope is removable from the controller and disposable, and wherein the controller is reusable.

8. The endoscope system of claim 1, wherein the display screen comprises a touch screen, and wherein the controller further comprises instructions for steering the distal end in response to an input from the user on the touch screen.

9. The endoscope system of claim 1, wherein the handheld controller comprises a video laryngoscope.

10. An endoscope system, comprising:
an endoscope comprising a working channel and a steerable distal end with a camera and an orientation sensor;
a controller in communication with the endoscope and comprising a display screen; and
a user interface (UI) presented on the display screen, wherein the UI comprises:
a window displaying a view from the camera;
a first orientation icon visually representing a first orientation of the steerable distal end;
a second orientation icon visually representing a first articulation of the steerable distal end;
a working-channel indicator representative of a rotational orientation of the working channel of the endoscope; and
a touch interface for receiving a touch input from a user;
wherein the controller comprises a hardware memory storing instructions for:
detecting, based on signals from the orientation sensor in the steerable distal end, a change to a second orientation and a second articulation of the steerable distal end of the endoscope;
modifying the first orientation icon and the working-channel indicator to visually represent the second orientation; and
modifying the second orientation icon to visually represent the second articulation.

11. The endoscope system of claim 10, wherein the first orientation icon comprises one or more of a roll indicator, a yaw indicator, and a pitch indicator.

12. The endoscope system of claim 10, wherein the first orientation icon comprises horizon markers.

13. The endoscope system of claim 10, wherein the steerable distal end is actively steerable within a range of motion having a limit, and wherein modifying the first orientation icon comprises visually changing the icon when the limit is reached.

14. The endoscope system of claim 13, wherein the controller further comprises a haptic generator, and wherein the stored instructions further comprise providing a haptic response when the limit is reached.

15. The endoscope system of claim 10, wherein the second orientation icon is a graphic of the steerable distal end that shows a current orientation and articulation state of the distal end.

16. The endoscope system of claim 1, wherein the graphical working-channel indicator is displayed as an overlay over the view from the camera.

17. The endoscope system of claim 16, wherein the graphical working-channel indicator is a partially transparent shaded region.

18. A visualization system comprising:
an endoscope comprising a steerable distal end that includes a camera and an orientation sensor; and
a video laryngoscope in communication with the endoscope and comprising a display screen and a hardware memory storing instructions for:
concurrently displaying on the display screen:
a view from the camera;
a first graphical orientation indicator representing an orientation of the steerable distal end of the endoscope;
a second graphical orientation indicator visually representing an articulation of the steerable distal end; and
a graphical working-channel indicator representative of a rotational orientation of a working channel of the endoscope;
based on signals from the orientation sensor in the steerable distal end:
detecting movement of the steerable distal end of the endoscope;
maintaining a rotational orientation of the view from the camera displayed on the display screen; and
modifying the first graphical orientation indicator, the second graphical orientation indicator, and the graphical working-channel indicator.

19. The visualization system of claim 18, wherein the graphical working-channel indicator is displayed as an overlay over the view from the camera.

20. The visualization system of claim 18, wherein the second orientation indicator is a graphic of the steerable distal end that shows a current articulation state and orientation of the distal end.

* * * * *